US010342718B2

(12) United States Patent
Watanabe

(10) Patent No.: US 10,342,718 B2
(45) Date of Patent: Jul. 9, 2019

(54) ABSORBENT ARTICLE

(71) Applicant: DAIO PAPER CORPORATION, Ehime (JP)

(72) Inventor: Yurie Watanabe, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 206 days.

(21) Appl. No.: 15/316,875

(22) PCT Filed: Jun. 11, 2015

(86) PCT No.: PCT/JP2015/066846
§ 371 (c)(1),
(2) Date: Dec. 7, 2016

(87) PCT Pub. No.: WO2015/190549
PCT Pub. Date: Dec. 17, 2015

(65) Prior Publication Data
US 2017/0135873 A1    May 18, 2017

(30) Foreign Application Priority Data

Jun. 13, 2014 (JP) .................................. 2014-122041

(51) Int. Cl.
*A61F 13/15*    (2006.01)
*A61F 13/539*    (2006.01)
(Continued)

(52) U.S. Cl.
CPC ............ *A61F 13/539* (2013.01); *A61F 13/15* (2013.01); *A61F 13/47* (2013.01); *A61F 13/51* (2013.01);
(Continued)

(58) Field of Classification Search
CPC ........ A61F 13/539; A61F 13/47; A61F 13/51; A61F 2013/4708; A61F 2013/51078; A61F 2013/53908
See application file for complete search history.

(56) References Cited

U.S. PATENT DOCUMENTS 5,891,118 A    4/1999    Toyoshima et al.
2003/0139719 A1    7/2003    Nanaurni et al.
(Continued)

FOREIGN PATENT DOCUMENTS

JP    H09-168563    6/1997
JP    2001-224629    8/2001
(Continued)

OTHER PUBLICATIONS

International Search Report dated Sep. 1, 2015.

*Primary Examiner* — Jacqueline F Stephens
(74) *Attorney, Agent, or Firm* — IPUSA, PLLC

(57) ABSTRACT

An incontinence pad (1) includes a permeable front-side sheet (3), a back-side sheet (2), an absorber (4) enveloped by an enveloping sheet (5) and disposed between the permeable front-side sheet and the back-side sheet, and an embossment (10) formed in a front surface of the permeable front-side sheet (3). An overlapped portion (9) is formed on a front side of the absorber (4) along a longitudinal direction by overlapping the side portions of the enveloping sheet (5), and at least a part of the embossment (10) overlaps the overlapped portion (9). An adhesive for bonding the side portions of the enveloping sheet (5) is not applied to a longitudinal area of the overlapped portion (9) where the embossment (10) is formed.

6 Claims, 7 Drawing Sheets

(51) Int. Cl.
*A61F 13/47* (2006.01)
*A61F 13/51* (2006.01)

(52) U.S. Cl.
CPC ............... *A61F 2013/4708* (2013.01); *A61F 2013/51078* (2013.01); *A61F 2013/53908* (2013.01)

(56) References Cited

U.S. PATENT DOCUMENTS

2011/0251575 A1* 10/2011 Kuroda ............... A61F 13/4704
 604/380
2013/0123729 A1* 5/2013 Minami .............. A61F 13/4756
 604/380

FOREIGN PATENT DOCUMENTS

| JP | 2001-276118 | 10/2001 |
| JP | 2003-284743 | 10/2003 |
| JP | 2006-141721 | 6/2006 |
| JP | 2015-100547 | 6/2015 |

* cited by examiner

ABSORBENT ARTICLE

TECHNICAL FIELD

The present invention relates to absorbent articles such as a sanitary napkin, a pantyliner, and an incontinence pad for absorbing, for example, menstrual blood and a vaginal discharge. More particularly, the present invention relates to an absorbent article including an absorber enveloped by an enveloping sheet and embossments formed on its front side.

BACKGROUND ART

There exists an absorbent article such as a pantyliner, a sanitary napkin, or an incontinence pad that is made by sandwiching an absorber, which is made of cellulose wadding such as ground pulp, a super absorbent polymer, or artificial fibers, between an impermeable back-side sheet such as a polyethylene sheet or a polyethylene-sheet-laminated nonwoven fabric and a permeable front-side sheet such as a nonwoven fabric or a permeable plastic sheet.

The absorber is enveloped in various manners with an enveloping sheet such as crepe paper or nonwoven fabric to maintain the shape of the absorber and to improve the diffusibility of a body fluid in the absorber. For example, Patent Document 1 discloses a rectangular absorber made by enveloping an absorber core composed mainly of cotton-like pulp with tissue paper. Deep circular embossments are formed on the tissue paper on the front side of the absorber. The embossments are dispersed and distributed over at least the entire central area of the absorber. Also, Patent Document 2 discloses an absorbent article including an oblong absorber whose absorbing layer includes functional particles that give a particular function to the absorbent article, and a covering sheet that covers the entire absorber. The side portions of the covering sheet along the longitudinal direction of the absorber are overlapped with each other to cover the entire absorber. Portions of the covering sheet covering the upper and lower surfaces of the absorber extend beyond the front and rear ends of the absorber, and the upper and lower extending portions of the covering sheet are joined together to seal the entire absorber in the covering sheet.

RELATED-ART DOCUMENTS

Patent Documents

Patent Document 1: Japanese Laid-Open Patent Publication No. 2003-284743

Patent Document 2: Japanese Laid-Open Patent Publication No. 2001-276118

DISCLOSURE OF INVENTION

Problems to be Solved by the Invention

With the absorber of Patent Document 1, however, an overlapped portion formed by overlapping the side portions in the width direction of the tissue paper cannot be sealed unless the embossments are formed on the tissue paper to cover a certain proportion of the overlapped portion. As a result, the overlapped portion may open when the absorbent article is worn, and fibers (pulp, artificial fibers, or a mixture of pulp and artificial fibers) and super absorbent polymers in the absorbent core may spill out through the opening.

Also, with the absorbent article of Patent Document 2, because the covering sheet and the absorber are partially bonded together with, for example, a hot-melt adhesive, the bonded parts function as walls that inhibit the diffusion of the body fluid and reduce the absorption speed of the body fluid.

One object of the present invention is to provide an absorbent article configured such that an overlapped portion formed by overlapping the side portions of an enveloping sheet for enveloping an absorber does not easily open, and a fluid can smoothly diffuse in the absorber.

Means for Solving the Problems

To solve the above problems, the invention of claim 1 provides an absorbent article that includes a permeable front-side sheet; a back-side sheet; an absorber enveloped by an enveloping sheet and disposed between the permeable front-side sheet and the back-side sheet; and an embossment formed in a front surface of the permeable front-side sheet. An overlapped portion is formed on a front side of the absorber along a longitudinal direction by overlapping side portions of the enveloping sheet. At least a part of the embossment overlaps the overlapped portion, and an adhesive for bonding the side portions of the enveloping sheet is not applied to a longitudinal area of the overlapped portion where the embossment is formed.

According to the invention of claim 1, an overlapped portion is formed on a front side of the absorber along a longitudinal direction by overlapping side portions of the enveloping sheet enveloping the absorber, and at least a part of the embossment formed in the front surface of the permeable front-side sheet overlaps the overlapped portion. Forming the embossment to overlap the overlapped portion makes it possible to securely seal the overlapped portion of the enveloping sheet, and thereby makes it possible to prevent the overlapped portion from opening when the absorbent article is worn. Accordingly, this configuration makes it possible to prevent fibers (pulp, artificial fibers, or a mixture of pulp and artificial fibers) and a super absorbent polymer in the absorber from spilling out through the opening.

Also, in the incontinence pad of the present invention, an adhesive for bonding the side portions of the enveloping sheet is not applied to a longitudinal area of the overlapped portion where the embossment is formed. This configuration prevents the adhesive from inhibiting the diffusion of a body fluid, allows the body fluid to diffuse in a wider area, and makes it possible to absorb and retain the body fluid in a wider area of the absorber.

The invention of claim 2 provides the absorbent article of claim 1 where the embossment includes bilaterally-symmetrical embossments that are symmetrical with respect to a longitudinal center line of the absorbent article, and the longitudinal length of at least one of the bilaterally-symmetrical embossments that overlaps the overlapped portion is greater than or equal to 70% of the longitudinal length of the overlapped portion.

According to the invention of claim 2, the longitudinal length of at least one of the bilaterally-symmetrical embossments that overlaps the overlapped portion is greater than or equal to 70% of the longitudinal length of the overlapped portion. This configuration makes it possible to reliably prevent the overlapped portion from opening.

The invention of claim 3 provides the absorbent article of claim 1 or 2 where the embossment includes bilaterally-symmetrical embossments that are symmetrical with respect to a longitudinal center line of the absorbent article, and the lateral length of at least one of the bilaterally-symmetrical embossments that overlaps the overlapped portion is greater than or equal to 10% of the lateral length of the overlapped portion.

According to the invention of claim 3, the lateral length of at least one of the bilaterally-symmetrical embossments that overlaps the overlapped portion is greater than or equal to 10% of the lateral length of the overlapped portion. This configuration makes it possible to more reliably prevent the overlapped portion from opening.

The invention of claim 4 provides the absorbent article of any one of claims 1 through 3 where one embossment or multiple embossments that are apart from each other in a width direction are formed on each of right and left sides of the absorbent article.

The invention of claim 4 defines that either one embossment or multiple embossments apart from each other in the width direction may be formed on each of the right and left sides of the absorbent article. Forming multiple embossments on each side makes it possible to more reliably prevent the overlapped portion from opening, facilitates the penetration of the body fluid through the embossments into the absorber, and enables the body fluid to be quickly absorbed by the absorber.

The invention of claim 5 provides the absorbent article of any one of claims 1 through 4 where the embossment is formed as a continuous line or a broken line.

According to the invention of claim 5, the embossment may be formed as a continuous line. This configuration makes it possible to more reliably prevent the overlapped portion from opening, and improves the diffusibility of the body fluid in the longitudinal direction. Also, the embossment may be formed as a broken line where compressed parts and non-compressed parts are alternately arranged.

The invention of claim 6 provides the absorbent article of any one of claims 1 through 5 where the adhesive for bonding the side portions of the enveloping sheet is applied to areas of the overlapped portion that are located further outside in the longitudinal direction than the longitudinal area of the overlapped portion where the embossment is formed.

According to the invention of claim 6, the adhesive for bonding the side portions of the enveloping sheet is applied to areas of the overlapped portion that are located further outside in the longitudinal direction than the longitudinal area of the overlapped portion where the embossment is formed. This configuration makes it possible to prevent the longitudinal ends of the overlapped portion from opening.

Advantageous Effect of the Invention

As described above, the present invention makes it possible to provide an absorbent article configured such that an overlapped portion formed by overlapping the side portions of an enveloping sheet for enveloping an absorber does not easily open, and a fluid can smoothly diffuse in the absorber.

DESCRIPTION OF EMBODIMENTS

Embodiments of the present invention are described below with reference to the accompanying drawings.

Figure 1:
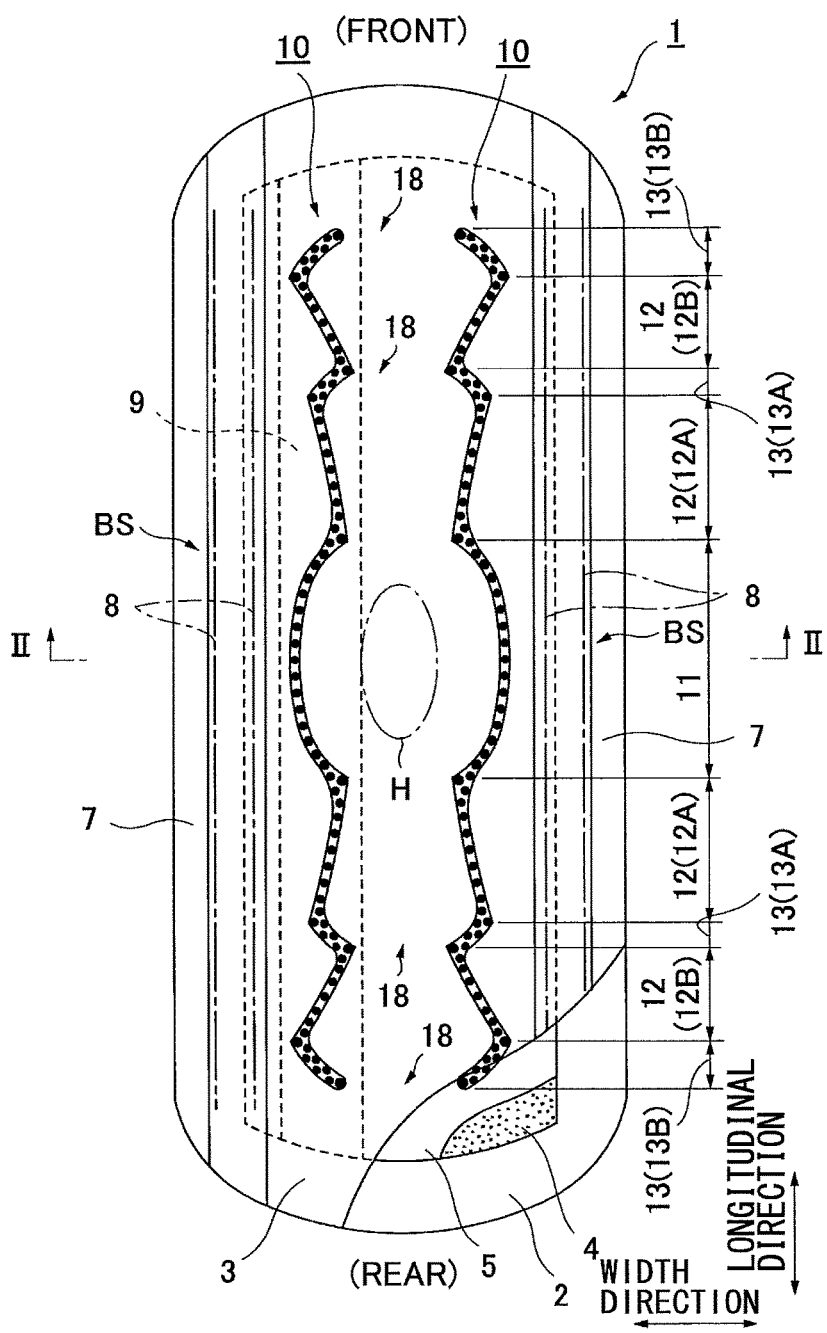
FIG. 1 is a partially cut-away view of an incontinence pad 1 according to the present invention.
Figure 2:
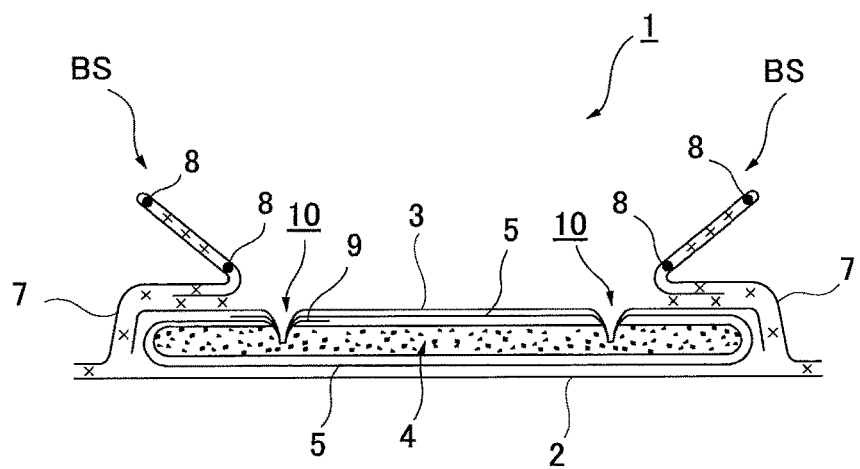
FIG. 2 is a cross-sectional view taken along line II-II of FIG. 1.

As illustrated by FIGS. 1 and 2, an incontinence pad 1 of the present invention includes an impermeable back-side sheet 2 such as a polyethylene sheet; a permeable front-side sheet 3 that allows, for example, urine to quickly pass through; an absorber 4 sandwiched between the sheets 2 and 3 and made of, for example, cotton-like pulp or synthetic pulp; an enveloping sheet 5 that is made of, for example, crepe paper or nonwoven fabric and envelops the absorber 4 to maintain the shape of the absorber 4 and to improve the diffusibility of the absorber 4; and side nonwoven fabrics 7 forming a pair of right and left solid gathers BS that rise from positions near the side edges of the absorber 4 toward the skin, and extend in the longitudinal direction across a predetermined area to cover at least a body-fluid ejection part H. At the end edges of the absorber 4 in the longitudinal direction, the outer edges of the impermeable back-side sheet 2 and the permeable front-side sheet 3 are bonded together with an adhesive such as a hot melt or by a bonding technique such as heat sealing. Also, at the side edges of the absorber 4, parts of the impermeable back-side sheet 2 extending laterally beyond the absorber 4 are bonded to the side nonwoven fabrics 7 with an adhesive such as a hot melt or by a bonding technique such as heat sealing. Also, as necessary, a hydrophilic second sheet (not shown) may be provided between the permeable front-side sheet 3 and the absorber 4.

The structure of the incontinence pad 1 is described in more detail below.

The impermeable back-side sheet 2 may be made of a sheet material such as polyethylene or polypropylene having at least a waterproof property. Also, a nonwoven fabric sheet that is made substantially impermeable by using a waterproof film (i.e., an impermeable back-side sheet including a waterproof film and a nonwoven fabric) may be used as the impermeable back-side sheet 2. In recent years, sheets having vapor permeability have been preferably used to prevent stuffiness. As a waterproof and vapor-permeable sheet, a microporous sheet is preferably used. A microporous sheet is obtained by melt-mixing an inorganic filler with an olefin resin such as polyethylene or polypropylene to form a sheet, and by stretching the sheet uniaxially or biaxially.

The permeable front-side sheet 3 is preferably made of a porous or nonporous nonwoven fabric or a porous plastic sheet. Examples of fiber materials of the nonwoven fabric include synthetic fibers made of olefin such as polyethylene or polypropylene, polyester, or polyamide; regenerated fibers such as rayon and cupra, and natural fibers such as cotton. The nonwoven fabric may be produced by any appropriate production method such as a spun lace method, a spun bond method, a thermal bond method, a melt blown method, or a needle punching method. Among these production methods, the spun lace method has an advantage in terms of flexibility and draping characteristics, and the thermal bond method has an advantage in terms of bulkiness and softness.

The absorber 4 may include, for example, absorbent fibers such as fluff pulp and a super absorbent polymer. In the example of FIG. 1, the absorber 4 has a substantially-oval shape in plan view that is long in the longitudinal direction of the incontinence pad 1. The super absorbent polymer is in the form of, for example, a granular powder, and is dispersed and mixed in pulp constituting the absorber 4.

The pulp may be made of cellulose fibers such as chemical pulp and dissolving pulp made from wood, or synthetic cellulose fibers such as rayon and acetate. In terms of the function and the price, softwood pulp with a long fiber length is more preferable than hardwood pulp. The mass per unit area of the pulp is between 100 $g/m^2$ and 600 $g/m^2$, and is preferably between 150 $g/m^2$ and 400 $g/m^2$.

Examples of the super absorbent polymer include crosslinked polyacrylate, self-crosslinked polyacrylate, saponified product of crosslinked acrylate-vinyl acetate copolymer, crosslinked isobutylene-maleic anhydride copolymer, crosslinked polysulfonate, and partially-crosslinked water-swellable polymer such as polyethylene oxide or polyacrylamide. Among them, polymers including acrylic acid or acrylate are preferable in terms of the water absorption amount and the water absorption rate. The water absorbing power (absorption ratio) and the water absorption rate of the super absorbent polymer can be adjusted by adjusting the crosslink density and the crosslink density gradient during the production process. The mass per unit area of the super absorbent polymer is between 60 $g/m^2$ and 400 $g/m^2$, and is preferably between 100 $g/m^2$ and 300 $g/m^2$ in order to give a predetermined absorption capacity to the body-fluid ejection part and an area around the body-fluid ejection part.

Synthetic fibers may also be added to the absorber 4. The synthetic fibers may be made of, for example, polyolefin such as polyethylene or polypropylene, polyester such as polyethylene terephthalate or polybutylene terephthalate, polyamide such as nylon, or a copolymer of these polymers. Also, a mixture of two types of synthetic fibers may be used. Further, bicomponent fibers may be used. Examples of bicomponent fibers include a core-in-sheath fiber including a high-melting-point fiber as a core and a low-melting-point fiber as a sheath, a side-by-side fiber, and a split fiber. When using hydrophobic synthetic fibers, the synthetic fibers are preferably surface-treated with a hydrophilic agent so that the synthetic fibers have an affinity to the body fluid.

The absorber 4 may include a base portion and a medium-height portion where the amounts of pulp and polymer are greater than those in the base portion. Also, a polymer sheet may be provided in a portion of the absorber 4. When the absorber 4 includes the medium-height portion, embossments 10 described later are preferably formed outside of the medium-height portion.

The absorber 4 is enveloped by the enveloping sheet 5. The enveloping sheet 5 may be made of a paper material such as tissue paper or a permeable sheet such as a nonwoven fabric. The mass per unit area of the enveloping sheet 5 is preferably between 10 $g/m^2$ and 50 $g/m^2$. Crepe paper is preferably used as the enveloping sheet 5 to allow the body fluid to easily diffuse in the entire absorber. The mass per unit area of the crepe paper is preferably between 13 $g/m^2$ and 18 $g/m^2$.

Figure 3:
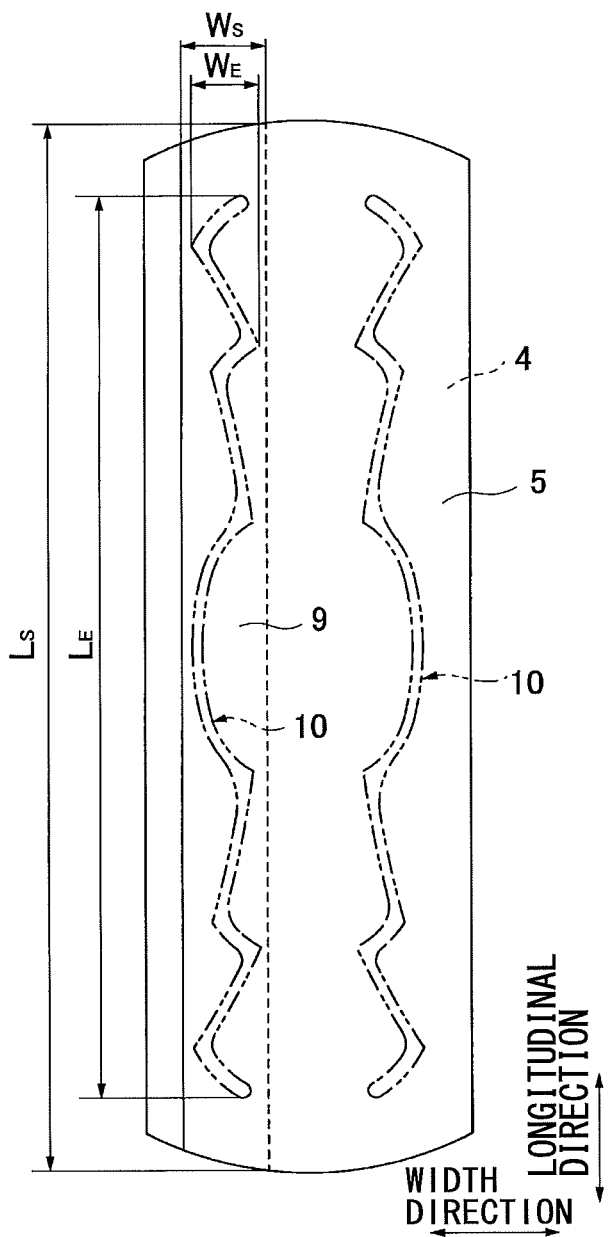
FIG. 3 is a plan view of an absorber 4 enveloped by a enveloping sheet 5.

The enveloping sheet 5 is placed on the back side (the side facing the impermeable back-side sheet 2) of the absorber 4, and the side portions of the enveloping sheet 5 are folded around the sides of the absorber 4 and are overlapped with each other on the front side (the side facing the permeable front-side sheet 3) of the absorber 4 to form an overlapped portion 9 having a predetermined width and extending across the entire length of the incontinence pad 1 in the longitudinal direction. As illustrated in FIG. 3, a width WS of the overlapped portion 9 is preferably between about 8 mm and about 14 mm.

The overlapped portion 9 is formed at a position that is offset from the center in the width direction of the absorber 4 toward one side (in the example of FIG. 3, the left side) of the absorber 4. At the overlapped portion 9, the side portions of the enveloping sheet 5 may be overlapped in any order. However, as illustrated in FIG. 3, the side portions of the enveloping sheet 5 are preferably overlapped such that one side portion extending toward the center in the width direction (the side portion folded around the left side of the absorber 4 in FIG. 3) becomes the lower layer, and another side portion extending outward in the width direction (the side portion folded around the right side of the absorber 4) becomes the upper layer. With this configuration, even when the overlapped portion 9 opens, the fibers (pulp, artificial fibers, or a mixture of pulp and artificial fibers) and the super absorbent polymer in the absorber 4 spill out sideways and do not easily enter the center portion of the incontinent pad 1. Accordingly, this configuration can reduce discomfort in wearing the incontinent pad 1.

In the examples of FIGS. 1 and 3, the outer edges of the enveloping sheet 5 matches the longitudinal ends of the absorber 4. However, the enveloping sheet 5 may extend outward beyond the longitudinal ends of the absorber 4.

In the incontinence pad 1, the absorber 4 is enveloped by the enveloping sheet 5, and therefore the enveloping sheet 5 exists between the permeable front-side sheet 3 and the absorber 4. The highly-absorbent enveloping sheet 5 causes a body fluid such as urine to quickly diffuse and prevents the backflow of the body fluid.

The side nonwoven fabrics 7 are provided on the front side of the incontinence pad 1. The side nonwoven fabrics 7 extend in the longitudinal direction along the sides of the incontinence pad 1 and across the entire length of the incontinence pad 1. The peripheral parts of the side nonwoven fabrics 7 extend laterally, and the peripheral parts of the impermeable back-side sheet 2 also extend laterally. The peripheral parts of the side nonwoven fabrics 7 and the impermeable back-side sheet 2 are joined together with, for example, a hot-melt adhesive to form side flaps.

For the side nonwoven fabrics 7, a water-repellent nonwoven fabric or a hydrophilic nonwoven fabric may be used depending on the priorities of functions of the side nonwoven fabrics 7. For example, when priority is given to a function to prevent penetration of, e.g., urine or a function to improve the feel, a water-repellent nonwoven fabric such as SSMS, SMS, or SMMS coated with a silicon-, paraffin-, or alkyl chromic chloride-water repellent is preferably used. When priority is given to the absorbency of a body fluid, a hydrophilic nonwoven fabric is preferably used. For example, such a hydrophilic nonwoven fabric may be prepared by polymerizing a compound having a hydrophilic group such as an oxidation product of polyethylene glycol during the production process of synthetic fibers. Also, a hydrophilic nonwoven fabric may be prepared by processing synthetic fibers with metal salt such as stannic chloride to partially dissolve the surfaces of the synthetic fibers and give them porosity, and by depositing metal hydroxide on the synthetic fibers. The resulting synthetic fibers become swollen or porous and exhibit a hydrophilic property due to capillarity. The side nonwoven fabrics 7 may be produced using natural fibers, synthetic fibers, or regenerated fibers as a material according to any appropriate production method.

As illustrated in FIG. 2, an outer portion of the side nonwoven fabric 7 relative to its center in the width direction is bonded with an adhesive such as a hot melt to an area that extends from an inner position on the absorber 4, slightly beyond the side edge of the absorber 4, to the outer edge of the impermeable back-side sheet 2. On the other hand, an inner portion of the side nonwoven fabric 7 is folded back in the width direction. At least the end portion of the folded-back portion has a double-sheet structure. At least one, in this example, two elastic strings 8 are provided in the double-sheet structure. The elastic strings 8 are fixed at the ends or at any appropriate positions in the longitudinal direction. The ends of the folded-back portion in the napkin's longitudinal direction are bonded to a lower layer. As illustrated in FIG. 2, the middle portion of the folded-back portion in the napkin's longitudinal direction including the elastic strings 8 is raised due to the contraction of the elastic strings 8 and forms the solid gather BS on the front side.

In the incontinence pad 1, as illustrated in FIG. 1, right and left embossments 10 are formed symmetrically with respect to the pad's longitudinal center line in the front surface of the permeable front-side sheet 3. One of the embossments 10 is formed in an area over the overlapped portion 9 of the enveloping sheet 5. After the absorber 4 is enveloped by the enveloping sheet 5 and the permeable front-side sheet 3 is stacked on the front side (skin side) of the enveloping sheet 5, the embossments 10 are formed by compressing parts of the permeable front-side sheet 3, the enveloping sheet 5, and the absorber 4 together from the front surface of the permeable front-side sheet 3.

The embossments 10 may be formed in various shapes. For example, as illustrated in FIG. 1, each embossment 10 may include a body-fluid ejection part embossment 11, longitudinal embossments 12, and diagonal embossments 13. In the example of FIG. 1, the longitudinal embossments 12 include first longitudinal embossments 12A adjacent to the body-fluid ejection part embossment 11 (i.e., located at inner positions), and second longitudinal embossments 12B located farther from the center than the first longitudinal embossments 12A in the longitudinal direction. The diagonal embossments include first diagonal embossments 13A that extend from the outer ends of the first longitudinal embossments 12A, and second diagonal embossments 13B that extend from the outer ends of the second longitudinal embossments 12B.

A pair of body-fluid ejection part embossments 11 are formed in regions that include areas adjacent in the pad's width direction to the area corresponding to the body-fluid ejection part H. The body-fluid ejection part embossments 11 are embossed lines that extend along the longitudinal direction of the incontinence pad 1 and curve outward in the width direction of the incontinence pad 1. The body-fluid ejection part embossments 11 are apart from each other in the lateral direction. The body-fluid ejection part embossments 11 prevent laterally-outward diffusion of the body fluid that is absorbed by the absorber 4 between the right and left body-fluid ejection part embossments 11, and thereby prevent side leakage of the body fluid. Also, the body-fluid ejection part embossments 11 cause the body fluid, which flows laterally outward from the center of the front surface, to flow into grooves so that the body fluid is quickly absorbed by the absorber 4. The right and left body-fluid ejection part embossments 11 are apart from each other in the pad's width direction and are independent from each other. The body-fluid ejection part embossment 11 has a shape that curves outward in the width direction. That is, the longitudinal center portion of the body-fluid ejection part embossment 11 is located farther from the center in the width direction than the longitudinal ends of the body-fluid ejection part embossment 11. For example, the body-fluid ejection part embossment 11 may be shaped like an arc or an ellipse. The body-fluid ejection part embossment 11 is preferably symmetric with reference to the center in the longitudinal direction of the body-fluid ejection part embossment 11 so that the body fluid is diffused evenly in the longitudinal direction.

The longitudinal embossments 12 are pairs of embossed lines formed before and after the body-fluid ejection part embossments 11 along the longitudinal direction of the incontinence pad 1. The longitudinal embossments 12 in each pair are apart from each other in the lateral direction. The longitudinal embossments 12 prevent the body fluid in the absorber from diffusing in the pad's width direction and thereby prevent side leakage of the body fluid. Also, the longitudinal embossments 12 guide the body fluid to diffuse in the pad's longitudinal direction. Two or more pairs of the longitudinal embossments 12 are preferably formed before and after the body-fluid ejection part embossments 11. In the example of FIG. 1, two pairs of the longitudinal embossments 12 are formed before and after the body-fluid ejection part embossments 11. That is, the first longitudinal embossments 12A and the second longitudinal embossments 12B are arranged in this order from each side of the body-fluid ejection part embossments 11 (i.e., from the inside).

As illustrated in FIG. 1, the diagonal embossments 13 are pairs of bilaterally-symmetric embossed lines that extend from the outer ends of the longitudinal embossments 12 and are inclined toward the center in the width direction of the incontinence pad 1. The diagonal embossments 13 cause the body fluid diffusing outward along the longitudinal embossments 12 to flow toward the center in the width direction of the incontinence pad 1. Also, the diagonal embossments 13 can be used as a scale to measure the amount of the body fluid absorbed by the absorber 4. In the example of FIG. 1, the diagonal embossments 13 include the first diagonal embossments 13A that extend from the outer ends of the first longitudinal embossments 12A and are connected to the inner ends of the second longitudinal embossments 12B, and the second diagonal embossments 13B that extend from the outer ends of the second longitudinal embossments 12B.

In the incontinence pad 1 described above, the embossments 10 include the body-fluid ejection part embossments 11, the longitudinal embossments 12 that are formed along the pad's longitudinal direction before and after the body-fluid ejection part embossments 11, and the diagonal embossments 13 that extend from the outer ends of the longitudinal embossments 12 and are inclined toward the center in the pad's width direction. This configuration makes it possible to determine the degree of diffusion of the body fluid in the absorber by just visually examining the surface of the used incontinence pad 1 using the diagonal embossments 13 as a scale, and to select an appropriate pad size based on the determined degree of diffusion of the body fluid.

Also in the incontinence pad 1, gaps 18 are formed between the ends of the right and left diagonal embossments 13 that are apart from each other in the width direction. This configuration prevents the embossments 10 from inhibiting the diffusion of the body fluid in the longitudinal direction in the absorber, and makes it possible to accurately determine the state of diffusion of the body fluid in the absorber. Also, because the diffusion of the body fluid is not inhibited, the body fluid does not stay near the body-fluid ejection part, and uncomfortable stickiness can be reduced.

In the incontinence pad 1, as illustrated in FIG. 3, at least a part of one of the bilaterally-symmetric embossments 10

(the left embossment 10 in FIG. 3) is formed in an area over the overlapped portion 9 formed by overlapping the side portions of the enveloping sheet 5. The longitudinal length (the length in the pad's longitudinal direction) of the embossment over the overlapped portion 9 is greater than or equal to 70%, preferably between 85% and 100%, and more preferably between 85% and 90% of a longitudinal length LS of the overlapped portion 9. That is, as in FIG. 3, when LS indicates the length of the overlapped portion 9 in the longitudinal direction of the incontinence pad 1 and LE indicates the length of the embossment 10 over the overlapped portion 9 in the longitudinal direction of the incontinence pad 1, a ratio LE/LS is represented by $0.7 \leq LE/LS$, preferably by $0.8 \leq LE/LS \leq 1$, and more preferably by $0.8 \leq LE/LS \leq 0.9$.

Forming the embossment 10 to overlap with a predetermined proportion of the overlapped portion 9 makes it possible to securely seal the overlapped portion 9 of the enveloping sheet 5, and thereby makes it possible to prevent the overlapped portion 9 from opening when the incontinence pad 1 is worn. Accordingly, this configuration makes it possible to prevent the fibers (pulp, artificial fibers, or a mixture of pulp and artificial fibers) and the super absorbent polymer in the absorber 4 from spilling out through the opening. This in turn makes it possible to prevent discomfort in wearing the incontinent pad 1 due to the spilled-out super absorbent polymer and to maintain the absorption capacity of the absorber 4.

On the other hand, when the length of the embossment 10 over the overlapped portion 9 is less than 70% of the longitudinal length of the overlapped portion 9, the length of the embossment 10 in a compact-type incontinence pad may become less than the length of the body-fluid ejection part. As a result, the overlapped portion 9 tends to open at an outer position than the longitudinal end of the embossment 10, and the wear comfort may be reduced due to the super absorbent polymer spilled out through the opening.

Figure 8:
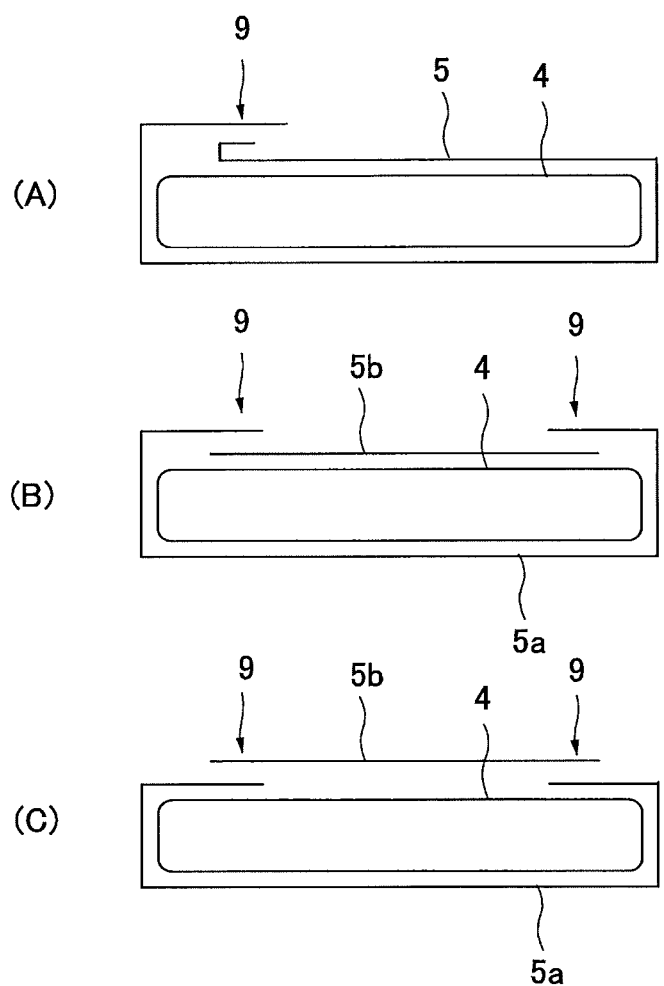
FIGS. 8 (A), 8 (B), and 8 (C) are cross-sectional views of the absorber 4 illustrating manners of enveloping the absorber 4 according to other embodiments.

As described later (FIGS. 8 (B) and 8 (C)), when the overlapped portion 9 is formed on each side of the absorber 4 and the embossment 10 is formed over each overlapped portion 9, the embossment 10 is formed such that its length becomes greater than or equal to a predetermined proportion of the length of the corresponding overlapped portion 9.

Figure 4:
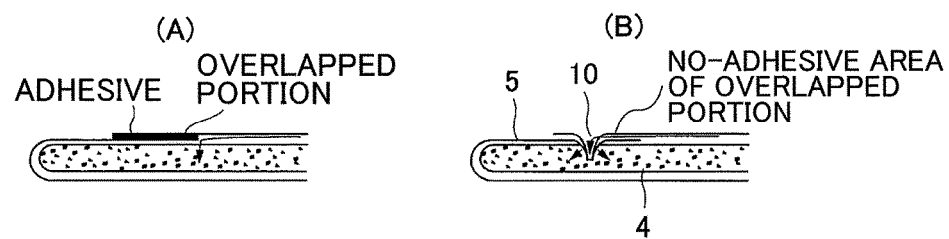
FIGS. 4 (A) and 4 (B) are enlarged cross-sectional views of the absorber 4 enveloped by the enveloping sheet 5.

Also, in the incontinence pad 1, no adhesive is used to join the side portions of the enveloping sheet 5 in a longitudinal area of the overlapped portion 9 where the embossment 10 is formed. That is, in an area corresponding to the longitudinal length LE of the embossment 10, the side portions of the enveloping sheet 5 forming the overlapped portion 9 are not joined by means other than the embossment 10. If the overlapped portion is bonded with an adhesive as illustrated by FIG. 4(A), the adhesive functions as a wall that blocks the body fluid diffusing laterally outward from the center. That is, the adhesive inhibits the diffusion of the body fluid in the laterally-outward direction, and prevents the body fluid from evenly absorbed and retained by the entire absorber. On the other hand, with the incontinence pad 1, as illustrated by FIG. 4 (B), no adhesive is applied to the overlapped portion 9 in the area where the embossment 10 is formed. This configuration makes it easier for the body fluid to diffuse in the width direction from the center, and enables the body fluid to be evenly absorbed and retained by the entire absorber 4.

Figure 5:
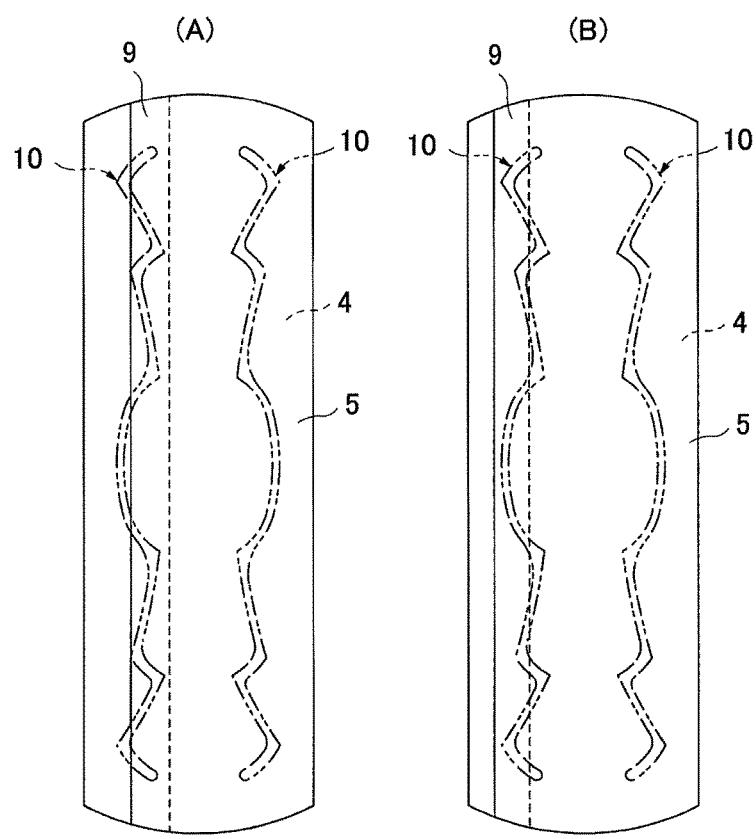
FIGS. 5 (A) and 5 (B) are plan views of the absorber 4 enveloped by the enveloping sheet 5.

As illustrated in FIG. 3, an embossment 10 of the bilaterally-symmetric embossments 10 formed over the overlapped portion 9 is preferably disposed in the center in the width direction of the overlapped portion 9 such that the entire embossment 10 extending in the longitudinal direction is within the area of the overlapped portion 9. This configuration makes it possible to securely seal the overlapped portion 9 with the entire embossment 10, and to reliably prevent the overlapped portion 9 from opening. On the other hand, when the embossment 10 is formed to zigzag in the pad's width direction, the embossment 10 may be formed such that parts of the embossment 10 protrude outward to cross the side edge of the upper layer of the overlapped portion 9 as illustrated by FIG. 5 (A), formed such that parts of the embossment 10 protrude inward to cross the side edge of the lower layer of the overlapped portion 9 as illustrated by FIG. 5 (B), or formed such that parts of the embossment 10 protrude outward and inward to cross the side edges of the upper and lower layers of the overlapped portion 9 (not shown). When the embossment 10 is formed to protrude from the overlapped portion 9, the embossment 10 is preferably formed such that parts of the embossment 10 cross the side edge of the upper layer of the overlapped portion 9 of the enveloping sheet 5 to more reliably prevent the upper layer of the overlapped portion 9 from peeling off and prevent the overlapped portion 9 from opening. When the embossment 10 is formed such that parts of the embossment 10 protrude from the overlapped portion 9, the total of the longitudinal lengths of other parts of the embossment 10 in the area of the overlapped portion 9 is preferably greater than or equal to 70% of the longitudinal length of the overlapped portion 9.

The lateral length (the length in the pad's width direction) of a part of the embossment 10 overlapping the overlapped portion 9 is greater than or equal to 10%, preferably between 40% and 70%, and more preferably 60% and 70% of a lateral length WS of the overlapped portion 9. That is, when WS indicates the lateral length of the overlapped portion 9 and WE indicates the lateral length of the embossment 10, a ratio WE/WS is represented by $0.1 \leq WE/WS$, preferably by $0.4 \leq WE/WS \leq 0.7$, and more preferably by $0.6 \leq WE/WS \leq 0.7$. This configuration makes it possible to more reliably prevent the overlapped portion 9 from opening.

The embossment 10 is preferably formed in the center in the longitudinal direction of the overlapped portion 9. That is, when the longitudinal length LE of the embossment 10 is less than the longitudinal length LS of the overlapped portion 9, the length between the front end of the embossment 10 and the front end of the overlapped portion 9 is preferably the same as the length between the rear end of the embossment 10 and the rear end of the overlapped portion 9. With this configuration, because a center portion in the longitudinal direction of the overlapped portion 9 is sealed by the embossment 10, it is possible to reliably prevent the center portion of the overlapped portion 9 corresponding to the body-fluid ejection part from opening. This in turn makes it possible to prevent the fibers (pulp, artificial fibers, or a mixture of pulp and artificial fibers) and the super absorbent polymer in the absorber 4 from spilling out through the opening, and makes it possible to prevent discomfort in wearing the incontinent pad 1 due to the spilled-out super absorbent polymer.

One embossment 10 may be formed on each of the right and left sides of the incontinence pad 1 as illustrated in FIG. 1. Also, multiple embossments 10 that are entirely (FIG. 6 (A)) or partially (FIG. 6 (B)) apart from each other in the width direction may be formed on each of the right and left sides of the incontinence pad 1. One to three embossments 10 are preferably formed on each of the right and left sides of the incontinence pad 1. Taking into account the effect of preventing side leakage and wearability, the maximum number of the embossments 10 on each side is more preferably two. Forming multiple embossments 10 on each side makes it possible to more reliably prevent the overlapped portion 9 from opening, facilitates the penetration of the body fluid through the embossments 10 into the absorber 4, and enables the body fluid to be quickly absorbed by the absorber 4.

Figure 6:
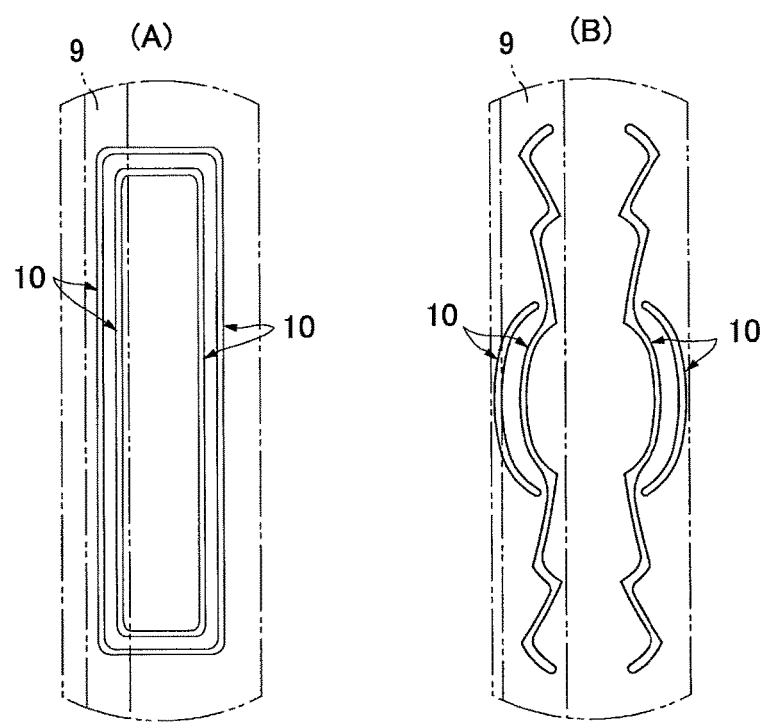
FIGS. 6 (A) and 6 (B) are plan views of embossments 10.

The planar shape of the embossment 10 may be a straight line as illustrated in FIG. 6 (A), a curved line, or a wavy line. Also, the embossment 10 may have a zigzag shape composed of multiple curved lines as illustrated in FIG. 1. The bilaterally-symmetric embossments 10 may be disposed apart from each other in the width direction as illustrated in FIG. 1. Also, the embossments 10 may be shaped like closed paths each of which is formed by connecting the longitudinal ends of straight lines. When the embossments 10 are shaped like closed paths, the whole or a part of an embossed line extending in the pad's longitudinal direction on one side in the width direction of the absorber 4 preferably has a length that is greater than or equal to 70% of the longitudinal length of the overlapped portion 9.

The embossment 10 may be formed as a continuous line or a broken line in the pad's longitudinal direction. The continuous line indicates a continuously-compressed embossment 10. The broken line indicates an embossment 10 where compressed parts and non-compressed parts are alternately arranged, i.e., where compressed parts are intermittently arranged. Forming the embossment 10 as a continuous line makes it possible to reliably seal the overlapped portion 9, and makes it easier to guide the body fluid in the pad's longitudinal direction along the continuous embossed line. On the other hand, forming the embossment 10 as a broken line makes it possible to prevent the incontinence pad 1 from becoming hard due to embossing, and to reduce discomfort in wearing the incontinence pad 1.

When the embossment 10 is formed as a broken line, the longitudinal length LE of the embossment 10 in FIG. 3 is represented by the distance between the front and rear ends of the embossment 10 including the non-compressed parts, and the embossment 10 is formed such that the longitudinal length LE becomes greater than or equal to 70% of the length LS of the overlapped portion 9. Also, when the embossment 10 is formed as a broken line composed of compressed parts and non-compressed parts, to securely seal the overlapped portion 9 with the compressed parts of the embossment 10, the embossment 10 is preferably formed such that the total of the longitudinal lengths of the compressed parts becomes greater than or equal to 40% of the length LS of the overlapped portion 9. Accordingly, in this case, the embossment 10 is formed such that the total longitudinal length of the compressed parts becomes greater than or equal to 57% of the total longitudinal length of the embossment 10.

When the embossment 10 is formed as a broken line composed of compressed parts and non-compressed parts, the distance between adjacent compressed parts (the length of each non-compressed part) is preferably set at a value less than or equal to 3 mm. With this configuration, the compression forces of the adjacent compressed parts influence each other and cause the non-compressed part between the adjacent compressed parts to be slightly indented from the surrounding non-compressed part. As a result, the body fluid can smoothly diffuse along the embossment 10 as if it is a continuous line. On the other hand, when the distance between adjacent compressed parts (the length of each non-compressed part) is set at a value greater than 3 mm, the diffusion of the body fluid along the embossment 10 is suppressed. As a result, the body fluid tends to accumulate at the ends of respective compressed parts and is absorbed by the absorber 4 via the compressed parts. Thus, this configuration facilitates the diffusion of the body fluid in the absorber 4.

Figure 7:
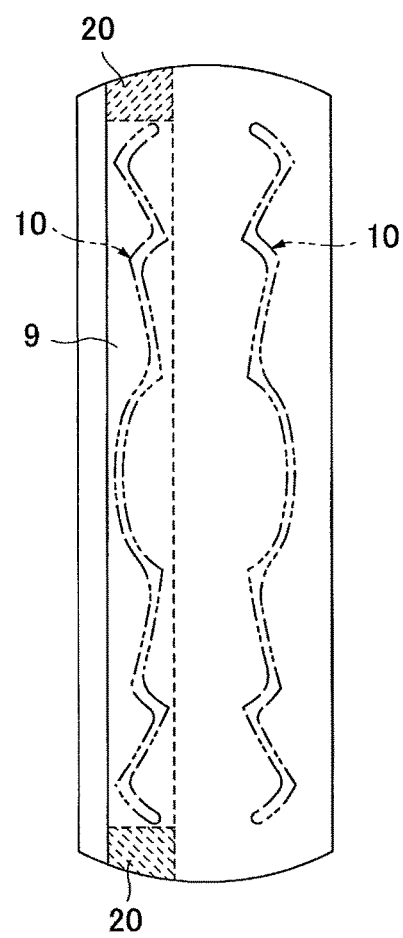
FIG. 7 is a plan view of the absorber 4 enveloped by the enveloping sheet 5.

As illustrated in FIG. 7, in the incontinence pad 1, adhesive application areas 20 may be provided at positions that are further outside in the longitudinal direction than the longitudinal ends of the embossment 10 formed over the overlapped portion 9. An adhesive such as a hot-melt adhesive is applied to the adhesive application areas 20 to bond the side portions of the enveloping sheet 5 forming the overlapped portion 9. In the example of FIG. 7, the adhesive application areas 20 extend, respectively, from the ends of the embossment 10 to the front and rear ends of the overlapped portion 9. In other words, a middle area in the longitudinal direction of the overlapped portion 9 where the embossment 10 is formed is set as a non-bonding area to which no adhesive is applied, and areas before and after the non-bonding area are set as the adhesive application areas 20 to which an adhesive is applied. Forming the adhesive application areas 20 makes it possible to prevent the opening of the longitudinal ends of the overlapped portion 9 that are located further outside than the outer ends of the embossment 10, and makes it possible to prevent the entire overlapped portion 9 from opening.

Other Embodiments (1) In the above embodiment, the embossment 10 is formed by compressing the permeable front-side sheet 3, the enveloping sheet 5, and the absorber 4 together from the front surface of the permeable front-side sheet 3. However, the embossment 10 may be formed after enveloping the absorber 4 with the enveloping sheet 5 and before stacking the permeable front-side sheet 3 by compressing the enveloping sheet 5 and the absorber 4 together from the front side (skin side) of the enveloping sheet 5.

(2) The absorber 4 may be enveloped with the enveloping sheet 5 in various manners. In the example of FIG. 8 (A), the end portion of the enveloping sheet 5 forming the lower layer of the enveloped portion 9 is folded back. In the example of FIG. 8 (B), two enveloping sheets 5a and 5b are used. The side portions of the enveloping sheet 5a placed on the back side of the absorber 4 are folded around the sides of the absorber 4 to reach intermediate positions on the front side of the absorber 4. Then, the enveloping sheet 5b is placed on the front side of the absorber 4 such that the side portions of the enveloping sheet 5b are located below the side portions of the enveloping sheet 5a (i.e., to face the absorber 4) and overlapped portions 9 are formed on the right and left sides of the absorber 4. In the example of FIG. 8 (C), similarly to the example of FIG. 8 (B), the side portions of the enveloping sheet 5b are placed over the side portions of the enveloping sheet 5a to form overlapped portions 9 on the right and left sides of the absorber 4. When the overlapped portions 9 are formed on the right and left sides of the absorber 4 as illustrated by FIGS. 8 (B) and 8 (C), each of the bilaterally-symmetric embossments 10 is preferably formed to overlap with a predetermined proportion of the corresponding one of the overlapped portions 9.

Explanation of Reference Numerals 1 incontinence pad, 2 impermeable back-side sheet, 3 permeable front-side sheet, 4 absorber, 5 enveloping sheet, 7 side nonwoven fabric, 8 elastic string, 9 overlapped portion, 10 embossment, 11 body-fluid ejection part embossment, 12 longitudinal embossment, 12A first longitudinal embossment, 12B second longitudinal embossment, 13 diagonal embossment, 13A first diagonal embossment, 13B second diagonal embossment, 20 adhesive application area

The invention claimed is:

1. An absorbent article, comprising:
    a permeable front-side sheet;
    a back-side sheet;
    an absorber enveloped by an enveloping sheet and disposed between the permeable front-side sheet and the back-side sheet; and
    an embossment formed in a front surface of the permeable front-side sheet,
   wherein
    an overlapped portion is formed on a front side of the absorber along a longitudinal direction by overlapping side portions of the enveloping sheet;
    at least a part of the embossment overlaps the overlapped portion; and
    parts of the side portions constituting the overlapped portion are bonded to each other with an adhesive, and no adhesive is applied to other parts of the side portions corresponding to a longitudinal area of the overlapped portion where the embossment is formed.

2. The absorbent article as claimed in claim 1, wherein the embossment includes bilaterally-symmetrical embossments that are symmetrical with respect to a longitudinal center line of the absorbent article; and
    a longitudinal length of at least one of the bilaterally-symmetrical embossments that overlaps the overlapped portion is greater than or equal to 70% of a longitudinal length of the overlapped portion.

3. The absorbent article as claimed in claim 1, wherein
    the embossment includes bilaterally-symmetrical embossments that are symmetrical with respect to a longitudinal center line of the absorbent article; and
    a lateral length of at least one of the bilaterally-symmetrical embossments that overlaps the overlapped portion is greater than or equal to 10% of a lateral length of the overlapped portion.

4. The absorbent article as claimed in claim 1, wherein one embossment or multiple embossments that are apart from each other in a width direction are formed on each of right and left sides of the absorbent article.

5. The absorbent article as claimed in claim 1, wherein the embossment is formed as a continuous line or a broken line.

6. The absorbent article as claimed in claim 1, wherein the parts of the side portions bonded to each other with the adhesive are located further outside in the longitudinal direction than the longitudinal area.

* * * * *